(12) United States Patent  
Kim (10) Patent No.: US 8,420,819 B2  
(45) Date of Patent: Apr. 16, 2013

(54) PROCESS FOR OPTIMIZING THE PARTICLE SIZE OF AN ACTIVE PHARMACEUTICAL INGREDIENT BY CRYSTALLIZATION

(75) Inventor: Soojin Kim, Demarest, NJ (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 299 days.

(21) Appl. No.: 12/788,562

(22) Filed: May 27, 2010

(65) Prior Publication Data

US 2010/0311978 A1    Dec. 9, 2010

Related U.S. Application Data

(60) Provisional application No. 61/183,615, filed on Jun. 3, 2009.

(51) Int. Cl.
*C07D 471/04* (2006.01)

(52) U.S. Cl.
USPC .......................................................... 546/113

(58) Field of Classification Search .................. 546/113
See application file for complete search history.

(56) References Cited

U.S. PATENT DOCUMENTS

| 6,903,215 B2 | 6/2005 | Betageri et al. |
| 2005/0176706 A1 | 8/2005 | Bekkali et al. |

FOREIGN PATENT DOCUMENTS

WO    2009/149139    * 12/2009

OTHER PUBLICATIONS

International Search Report for PCT/US2010/036503 mailed Aug. 24 2010.

* cited by examiner

*Primary Examiner* — Niloofar Rahmani
(74) *Attorney, Agent, or Firm* — Michael P. Morris; Timothy X. Witkowski; Usha R. Patel (57) ABSTRACT

A process to crystallize uniform small particles of a compound of Formula (I) with narrow particle size distribution and excellent powder characteristics that facilitate the formulation process and optimal drug product performance, wherein the compound of Formula (I) is:

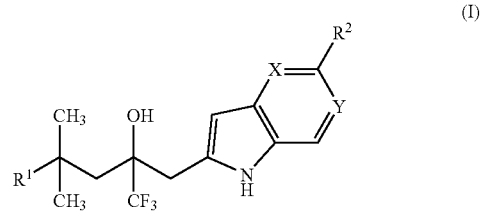

(I)

wherein $R^1$, $R^2$, and $R^3$ are as described herein.

32 Claims, 4 Drawing Sheets

PROCESS FOR OPTIMIZING THE PARTICLE SIZE OF AN ACTIVE PHARMACEUTICAL INGREDIENT BY CRYSTALLIZATION

FIELD OF THE INVENTION

The present invention relates to a method for optimizing the particle size of an active pharmaceutical ingredient (API) by crystallization that provides advantages over milling in terms of powder characteristics and particles uniformity.

BACKGROUND OF THE INVENTION

Crystallization is a critical operation in the manufacture of pharmaceutical compounds. The crystallization process as part of the synthesis of an API affects the API crystal properties such as purity, polymorphic form, and particle size. Optimization of the crystallization process is important for API product quality as well as for process efficiency and high yield. Crystal properties also significantly impact the downstream processing. Another important aspect of crystallization development involves particle engineering to obtain desired particle size to meet the biopharmaceutical performance requirements.

For poorly soluble compounds, it is imperative to have small particle size in order to obtain maximum surface area and thus dissolution rate, which is usually a critical factor in improving bioavailability. It is not common or straightforward to achieve particle size uniformly below 10-20 µm by crystallization. Hence, many compounds are jet-milled to 10-20 µm, an expensive and highly energy intensive operation. Furthermore, oftentimes milled particles show non-uniform particle size distribution, poor powder flow, and low bulk density which cause difficult powder handling, formulation blending, and poor product content uniformity of drug product.

SUMMARY OF THE INVENTION

This invention is a process to consistently crystallize uniform small particles of a compound of Formula (I) with narrow particle size distribution and excellent powder characteristics that facilitate the formulation process and optimal drug product performance. The compound of Formula (I) is (I)

wherein:

$R^1$ is an aryl or heteroaryl group, each optionally independently substituted with one, two, or three substituent groups selected from $C_1$-$C_5$ alkyl, aminocarbonyl, $C_1$-$C_5$ alkylaminocarbonyl, $C_1$-$C_5$ dialkylaminocarbonyl, aminosulfonyl, $C_1$-$C_5$ alkylaminosulfonyl, $C_1$-$C_5$ dialkylaminosulfonyl, halogen, hydroxyl, cyano, and $C_1$-$C_5$ alkylthio wherein the sulfur atom is optionally oxidized to a sulfoxide or sulfone;

$R^2$ is $C_1$-$C_5$ alkylthio wherein the sulfur atom is optionally oxidized to a sulfoxide or sulfone, optionally independently substituted with one, two, or three substituent groups selected from halogen, hydroxy, oxo, cyano, alkoxyalkyl, and aminocarbonyl;

X is CH or N; and
Y is CH or N,
wherein X and Y are not both CH,
or a tautomer, optical isomer, prodrug, co-crystal, or salt thereof.

Another aspect of the invention includes compounds of Formula (I) wherein:

$R^1$ is an aryl or heteroaryl group, each optionally independently substituted with one, two, or three substituent groups selected from $C_1$-$C_5$ alkyl, aminocarbonyl, $C_1$-$C_5$ alkylaminocarbonyl, $C_1$-$C_5$ dialkylaminocarbonyl, aminosulfonyl, $C_1$-$C_5$ alkylaminosulfonyl, $C_1$-$C_5$ dialkylaminosulfonyl, halogen, hydroxyl, cyano, and $C_1$-$C_5$ alkylthio wherein the sulfur atom is optionally oxidized to a sulfoxide or sulfone;

$R^2$ is $C_1$-$C_5$ alkylthio wherein the sulfur atom is optionally oxidized to a sulfoxide or sulfone, each optionally independently substituted with one to three substituent groups selected from halogen, hydroxy, oxo, cyano, alkoxyalkyl, and aminocarbonyl;

X is CH; and
Y is N,
or a tautomer, prodrug, co-crystal, or salt thereof.

Yet another aspect of the invention includes compounds of Formula (I) wherein:

$R^1$ is an aryl group, optionally substituted with one, two, or three substituent groups independently selected from $C_1$, $C_2$, or $C_3$ alkyl, aminocarbonyl, halogen, and $C_1$, $C_2$, or $C_3$ alkylthio wherein the sulfur atom is optionally oxidized to a sulfoxide or sulfone;

$R^2$ is $C_1$, $C_2$, or $C_3$ alkylthio wherein the sulfur atom is optionally oxidized to a sulfoxide or sulfone, each optionally independently substituted with one to three substituent groups selected from halogen, hydroxy, oxo, cyano, alkoxyalkyl, and aminocarbonyl;

X is CH; and
Y is N,
or a tautomer, prodrug, co-crystal, or salt thereof.

Yet another aspect of the invention includes compounds of Formula (I) wherein:

$R^1$ is a phenyl group, optionally substituted with one or two substituent groups independently selected from aminocarbonyl, methyl, fluoro, chloro, bromo, and $C_1$ or $C_2$ alkylthio wherein the sulfur atom is optionally oxidized to a sulfoxide or sulfone;

$R^2$ is $C_1$, $C_2$, or $C_3$ alkylthio wherein the sulfur atom is optionally oxidized to a sulfoxide or sulfone;

X is CH; and
Y is N,
or a tautomer, prodrug, co-crystal, or salt thereof.

Still another aspect of the invention includes compounds of Formula (I) wherein:

$R^1$ is a phenyl group, optionally substituted with one or two substituent groups independently selected from aminocarbonyl, methyl, fluoro, chloro, bromo, and $C_1$ or $C_2$ alkylthio wherein the sulfur atom is optionally oxidized to a sulfoxide or sulfone;

$R^2$ is $C_1$ or $C_2$ alkylthio wherein the sulfur atom is optionally oxidized to a sulfoxide or sulfone;

X is CH; and
Y is N,
or a tautomer, prodrug, co-crystal, or salt thereof.

Yet another aspect of the invention includes compounds of Formula (I) wherein the crystals of the compound of Formula (I) is 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid co-crystal, and other compounds mentioned herein.

The invention comprises a process for crystallizing a compound of Formula (I)

wherein:
$R^1$ is an aryl or heteroaryl group, each optionally independently substituted with one, two, or three substituent groups selected from $C_1$-$C_5$ alkyl, aminocarbonyl, $C_1$-$C_5$ alkylaminocarbonyl, $C_1$-$C_5$ dialkylaminocarbonyl, aminosulfonyl, $C_1$-$C_5$ alkylaminosulfonyl, $C_1$-$C_5$ dialkylaminosulfonyl, halogen, hydroxyl, cyano, and $C_1$-$C_5$ alkylthio wherein the sulfur atom is optionally oxidized to a sulfoxide or sulfone;

$R^2$ is $C_1$-$C_5$ alkylthio wherein the sulfur atom is optionally oxidized to a sulfoxide or sulfone, optionally independently substituted with one, two, or three substituent groups selected from halogen, hydroxy, oxo, cyano, alkoxyalkyl, and aminocarbonyl;

X is CH or N; and
Y is CH or N,
wherein X and Y are not both CH,
or any of the other compounds of Formula (I) disclosed herein, or a tautomer, optical isomer, prodrug, co-crystal, or salt thereof, the process comprising:
(a) dissolving the free base of the compound of Formula (I) in a primary organic solvent to obtain a first solution;
(b) adding an acid to the first solution to obtain a second solution;
(c) combining an organic antisolvent with the second solution to obtain a third solution, wherein the antisolvent is miscible with the primary organic solvent and in which the compound of Formula (I) has a lesser solubility than in the primary organic solvent;
(d) achieving supersaturation of the compound of Formula (I) in the third solution to obtain a supersaturated fourth solution; and
(e) obtaining crystals of the compound of Formula (I) or a tautomer, optical isomer, prodrug, co-crystal, or salt thereof.

In another aspect, the primary organic solvent is a polar organic solvent, for example, MEK, 2-butanone, acetic acid, or a mixture thereof, preferably MEK. In yet another aspect, the acid is a strong acid, preferably an inorganic acid, such as phosphoric acid. In an additional aspect, the organic antisolvent is a nonpolar organic solvent, such as an alkane or cycloalkane, preferably heptane, cyclohexane, methylcyclohexane, or butyl acetate. Preferably, the ratio of the solubility of the compound of Formula (I) in the primary organic solvent to organic antisolvent is, for example, at least 3:1; at least 5:1; at least 10:1; or at least 20:1.

In another aspect, steps (c) and (d) are achieved by adding the solution in step (b) to the organic antisolvent at a temperature of 0° C. to 40° C., and preferably the organic antisolvent includes seed crystals of the desired crystal structure of the compound of Formula (I). In another aspect, step (d) is achieved by one or more of the following: adding additional amounts of the organic antisolvent, reducing the temperature, and removing the primary organic solvent. In yet another aspect, step (e) is accomplished by introducing seed crystals to the supersaturated solution of step (d). In a further aspect, the process further comprises (f) adding additional antisolvent to increase the yield of the crystals of the compound of Formula (I) or a tautomer, optical isomer, prodrug, co-crystal, or salt thereof. In another aspect, the process occurs at a temperature of about 20° C. to about 60° C., about 40° C. to about 60° C., about 30° C. to about 50° C., about 50° C. to about the refluxing temperature of the fourth solution; or about 50° C.

In another aspect, the third solution includes water, preferably about 0.01 wt % to about 0.5 wt % water in the solution of compound of Formula (I), measured by Karl-Fischer titration (KF), or the water present is from about 0.5 wt % to about 1.2 wt %, or the water present is from about 1.2 wt % to about 2.0 wt %. In yet another aspect, the water present is selected so that the crystals of the compound of Formula (I) or a tautomer, optical isomer, prodrug, co-crystal, or salt thereof has a D90 of about 5 µm to about 80 µm, or about 10 µm to about 30 µm, or about 30 µm to about 70 µm, or any other particle size distribution value or range of values disclosed herein.

DETAILED DESCRIPTION OF THE INVENTION

Definition of Terms and Conventions Used
Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

A. Chemical Nomenclature, Terms, and Conventions
In the groups, radicals, or moieties defined below, the number of carbon atoms is often specified preceding the group, for example, $C_1$-$C_{10}$ alkyl means an alkyl group or radical having 1 to 10 carbon atoms. In general, for groups comprising two or more subgroups, the last named group is the radical attachment point, for example, "alkylaryl" means a monovalent radical of the formula Alk-Ar—, while "arylalkyl" means a monovalent radical of the formula Ar-Alk- (where Alk is an alkyl group and Ar is an aryl group). Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups.

The terms "alkyl" or "alkyl group" mean a branched or straight-chain saturated aliphatic hydrocarbon monovalent radical. This term is exemplified by groups such as methyl, ethyl, n-propyl, 1-methylethyl (isopropyl), n-butyl, n-pentyl, 1,1-dimethylethyl (ten-butyl), and the like. It may be abbreviated "Alk".

The terms "aminocarbonyl", "alkylaminocarbonyl" and "dialkylaminocarbonyl" mean a monovalent radical of the formula $R_2NC(O)$—, where each R is independently hydrogen or lower alkyl.

The terms "alkylamino" or "alkylamino group" mean a monovalent radical of the formula (Alk)NH—, where Alk is alkyl. Exemplary alkylamino groups include methylamino, ethylamino, propylamino, butylamino, tert-butylamino, and the like.

The terms "dialkylamino" or "dialkylamino group" mean a monovalent radical of the formula (Alk)(Alk)N—, where each Alk is independently alkyl. Exemplary dialkylamino groups include dimethylamino, methylethylamino, diethylamino, dipropylamino, ethylpropylamino, and the like.

The terms "substituted amino" or "substituted amino group" mean a monovalent radical of the formula —$NR_2$, where each R is independently a substituent selected from hydrogen or the specified substituents (but where both Rs cannot be hydrogen). Exemplary substituents include alkyl, alkanoyl, aryl, arylalkyl, cycloalkyl, heterocyclyl, heteroaryl, heteroarylalkyl, and the like.

The terms "halogen" or "halogen group" mean a fluoro, chloro, bromo, or iodo group.

The term "halo" means one or more hydrogen atoms of the group are replaced by halogen groups.

The terms "aryl" or "aryl group" mean an aromatic carbocyclic monovalent or divalent radical of from 6 to 14 carbon atoms having a single ring (e.g., phenyl or phenylene) or multiple condensed rings (e.g., naphthyl or anthranyl). Unless otherwise specified, the aryl ring may be attached at any suitable carbon atom which results in a stable structure and, if substituted, may be substituted at any suitable carbon atom which results in a stable structure. Exemplary aryl groups include phenyl, naphthyl, anthryl, phenanthryl, indanyl, indenyl, biphenyl, and the like. It may be abbreviated "Ar".

The terms "heteroaryl" or "heteroaryl group" mean a stable aromatic 5- to 14-membered, monocyclic or polycyclic monovalent or divalent radical which may comprise one or more fused or bridged ring(s), preferably a 5- to 7-membered monocyclic or 7- to 10-membered bicyclic radical, having from one to four heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heteroaryl ring may be attached at any suitable heteroatom or carbon atom which results in a stable structure and, if substituted, may be substituted at any suitable heteroatom or carbon atom which results in a stable structure. Exemplary and preferred heteroaryls include furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, triazinyl, indolizinyl, azaindolizinyl, indolyl, azaindolyl also known as pyrrolopyridinyl, diazaindolyl, dihydroindolyl, dihydroazaindoyl, isoindolyl, azaisoindolyl, benzofuranyl, furanopyridinyl, furanopyrimidinyl, furanopyrazinyl, furanopyridazinyl, dihydrobenzofuranyl, dihydrofuranopyridinyl, dihydrofuranopyrimidinyl, benzodioxolanyl, benzothienyl, thienopyridinyl, thienopyrimidinyl, thienopyrazinyl, thienopyridazinyl, dihydrobenzothienyl, dihydrothienopyridinyl, dihydrothienopyrimidinyl, indazolyl, azaindazolyl, diazaindazolyl, benzimidazolyl, imidazopyridinyl, benzthiazolyl, thiazolopyridinyl, thiazolopyrimidinyl, benzoxazolyl, oxazolopyridinyl, oxazolopyrimidinyl, benzisoxazolyl, purinyl, chromanyl, azachromanyl, quinolizinyl, quinolinyl, dihydroquinolinyl, tetrahydroquinolinyl, isoquinolinyl, dihydroisoquinolinyl, tetrahydroisoquinolinyl, cinnolinyl, azacinnolinyl, phthalazinyl, azaphthalazinyl, quinazolinyl, azaquinazolinyl, quinoxalinyl, azaquinoxalinyl, naphthyridinyl, dihydronaphthyridinyl, tetrahydronaphthyridinyl, pteridinyl, carbazolyl, acridinyl, phenazinyl, phenothiazinyl, and phenoxazinyl, and the like.

The term "compounds of Formula (I)" and equivalent expressions are mean to embrace compounds of Formula (I), either individually, in some combination, or all of them, as the context permits. Certain compounds of Formula (I) are disclosed in U.S. Pat. No. 6,903,215, U.S. Patent Application Publication No. 2005/0176706, U.S. Patent Application Publication No. 2009/0325988, and U.S. Application Ser. No. 61/059,388, filed Jun. 6, 2008, and these are each incorporated by reference in their entireties. In addition, synthetic methods of making the compounds of the invention are found, for example, in U.S. Application Ser. Nos. 61/183,601; 61/183,606; 61/183,607; and 61/183,610, each entitled Stereoselective Synthesis of Certain Trifluoromethyl-Substituted Alcohols and filed Jun. 3, 2009, each of which is incorporated by reference in their entireties.

The term "compounds of the invention" and equivalent expressions are meant to embrace compounds of Formula (I) as herein described, including the tautomers, the prodrugs, the co-crystals, or the salts, particularly the pharmaceutically acceptable salts, and the solvates and hydrates thereof, where the context so permits. In general and preferably, the compounds of the invention and the formulas designating the compounds of the invention are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits. Compounds of the invention as disclosed and claimed herein also are intended to include both compounds with normal (naturally-occurring) isotopic distributions of atoms as well as the corresponding isotopically-enriched compounds. Thus, unless otherwise stated, structures depicted herein are also meant to include compounds that differ only by being enriched with certain isotopes of a given atom. For example, compounds having the present structures except for the replacement of hydrogen ($^1H$) by deuterium ($^2H$) or tritium ($^3H$), or the replacement of a carbon by a $^{13}C$- or $^{14}C$-enriched carbon are within the scope of this invention. Examples of isotopes that can be incorporated into the compounds of the invention in accordance with well-established procedures include isotopes of hydrogen, carbon, nitrogen, oxygen, phosphorous, fluorine, and chlorine, for example, $^2H$, $^3H$, $^{13}C$, $^{14}C$, $^{15}N$, $^{18}O$, $^{17}O$, $^{31}O$, $^{32}P$, $^{35}S$, $^{18}F$, and $^{36}Cl$, respectively. Certain isotopically-labeled compounds described herein, for example, those into which radioactive isotopes such as $^3H$ and $^{14}C$ are incorporated, are useful in drug and/or substrate tissue distribution assays. Further, substitution with isotopes such as deuterium can afford certain therapeutic advantages resulting from greater metabolic stability, for example, increased in vivo half-life, lower toxicity, or reduced dosage requirements (see *Nature*, 458, 269 (2009)).

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The terms "stable compound" or "stable structure" mean a compound that is sufficiently robust to survive isolation to a useful degree of purity from a reaction mixture, and formulation into an efficacious therapeutic or diagnostic agent. For example, a compound which would have a "dangling valency" or is a carbanion is not a compound contemplated by the invention.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 R, then such group is optionally substituted with up to two R groups and R at each occurrence is selected independently from the defined list of possible R. Additionally, if a group is shown to be substituted with $C_1$-$C_5$ R group (e.g., $C_1$-$C_5$ alkylthio), then such group is optionally substituted with $C_1$, $C_2$, $C_3$, $C_4$, or $C_5$ R groups (e.g., $C_1$, $C_2$, $C_3$, $C_4$, or $C_5$ alkylthio). Such combinations of substituents and/or variables, however, are permissible only if such combinations result in stable compounds.

The yield of each of the reactions described herein is expressed as a percentage of the theoretical yield.

B. Co-Crystals, Salt, Prodrug, Derivative, and Solvate Terms and Conventions

The terms "prodrug" or "prodrug derivative" mean a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in *A Textbook of Drug Design and Development*, Krogsgaard-Larsen and H. Bundgaard (eds.), Gordon & Breach, 1991, particularly Chapter 5: "Design and Applications of Prodrugs"; *Design of Prodrugs*, H. Bundgaard (ed.), Elsevier, 1985; *Prodrugs: Topical and Ocular Drug Delivery*, K. B. Sloan (ed.), Marcel Dekker, 1998; *Methods in Enzymology*, K. Widder et al. (eds.), Vol. 42, Academic Press, 1985, particularly pp. 309-396; *Burger's Medicinal Chemistry and Drug Discovery*, 5th Ed., M. Wolff (ed.), John Wiley & Sons, 1995, particularly Vol. 1 and pp. 172-178 and pp. 949-982; *Pro-Drugs as Novel Delivery Systems*, T. Higuchi and V. Stella (eds.), Am. Chem. Soc., 1975; *Bioreversible Carriers in Drug Design*, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The term "salt" means an ionic form of the parent compound or the product of the reaction between the parent compound with a suitable acid or base to make the acid salt or base salt of the parent compound. Salts of the compounds of the present invention can be synthesized from the parent compounds which contain a basic or acidic moiety by conventional chemical methods. Generally, the salts are prepared by reacting the free base or acid parent compound with stoichiometric amounts or with an excess of the desired salt-forming inorganic or organic acid or base in a suitable solvent or various combinations of solvents.

The term "pharmaceutically acceptable salt" means a salt of a compound of the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the compounds of the present invention are useful in both free base and salt form, in practice, the use of the salt form amounts to use of the base form. Lists of suitable salts are found in, e.g., S. M. Birge et al., J. Pharm. Sci., 1977, 66, pp. 1-19, which is hereby incorporated by reference in its entirety.

The term "solvate" means a physical association of a compound with one or more solvent molecules or a complex of variable stoichiometry formed by a solute (for example, a compound of Formula (I)) and a solvent, for example, water, ethanol, or acetic acid. In certain instances, the solvate will be capable of isolation, for example, when one or more solvent molecules are incorporated in the crystal lattice of the crystalline solid. In general, the solvents selected do not interfere with the biological activity of the solute. Solvates encompasses both solution-phase and isolatable solvates. Representative solvates include hydrates, ethanolates, methanolates, and the like.

The term "co-crystal" means a crystalline material comprised of one or more compounds of the invention and one or more unique co-crystal formers which may include acidic, basic, or neutral molecules that are solids or liquids at room temperature. Accordingly, co-crystals encompass molecular compounds, molecular complexes, solvates, inclusion compounds, channel compounds, clathrates, and possibly other types of multi-component crystals.

The term "pharmaceutical co-crystal" means co-crystals that comprise one or more unique pharmaceutically acceptable co-crystal formers.

The compounds of the present invention as discussed below include the free base or acid thereof, their salts, co-crystals, and prodrugs and may include oxidized sulfur atoms or quaternized nitrogen atoms in their structure, although not explicitly stated or shown, particularly the pharmaceutically acceptable forms thereof. Such forms, particularly the pharmaceutically acceptable forms, are intended to be embraced by the appended claims.

C. Isomer Terms and Conventions

The term "isomers" means compounds having the same number and kind of atoms, and hence the same molecular weight, but differing with respect to the arrangement or configuration of the atoms in space. The term includes stereoisomers and geometric isomers.

The terms "stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the invention which may give rise to stereoisomerism, the invention contemplates stereoisomers and mixtures thereof. The compounds of the invention and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

The term "enantiomers" means a pair of stereoisomers that are non-superimposable mirror images of each other.

The terms "diastereoisomers" or "diastereomers" mean optical isomers which are not mirror images of each other.

The terms "racemic mixture" or "racemate" mean a mixture containing equal parts of individual enantiomers.

The term "non-racemic mixture" means a mixture containing unequal parts of individual enantiomers.

The term "geometrical isomer" means a stable isomer which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, C=N double bonds, cyclic structures, and the like may be present in the compounds of the invention, the invention contemplates each of the various stable geometric isomers and mixtures thereof resulting from the arrangement of substituents around these double bonds and in these cyclic structures. The substituents and the isomers are designated using the cis/trans convention or using the E or Z system, wherein the term "E" means higher order substituents on opposite sides of the double bond, and the term "Z" means higher order substituents on the same side of the double bond. A thorough discussion of E and Z isomerism is provided in J. March, *Advanced Organic Chemistry: Reactions, Mechanisms, and Structure*, 4th ed., John Wiley & Sons, 1992, which is hereby incorporated by reference in its entirety. Several of the following examples represent single E isomers, single Z isomers, and mixtures of E/Z isomers. Determination of the E and Z isomers can be done by analytical methods such as x-ray crystallography, $^1$H NMR, and $^{13}$C NMR.

Some of the compounds of the invention can exist in more than one tautomeric form. As mentioned above, the compounds of the invention include all such tautomers.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the invention from this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

Thus, if one enantiomer is pharmacologically more active, less toxic, or has a preferred disposition in the body than the other enantiomer, it would be therapeutically more beneficial to administer that enantiomer preferentially. In this way, the patient undergoing treatment would be exposed to a lower total dose of the drug and to a lower dose of an enantiomer that is possibly toxic or an inhibitor of the other enantiomer.

Preparation of Pure Enantiomers or Mixtures of Desired Enantiomeric Excess (Ee) or enantiomeric purity are accomplished by one or more of the many methods of (a) separation or resolution of enantiomers, or (b) enantioselective synthesis known to those of skill in the art, or a combination thereof. These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally in *Chiral Separation Techniques: A Practical Approach* (2nd Ed.), G. Subramanian (ed.), Wiley-VCH, 2000; T. E. Beesley and R. P. W. Scott, *Chiral Chromatography*, John Wiley & Sons, 1999; and Satinder Ahuja, *Chiral Separations by Chromatography*, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD ORD, X-ray crystallography, or NMR.

In general, all tautomeric forms and isomeric forms and mixtures, whether individual geometric isomers or stereoisomers or racemic or non-racemic mixtures, of a chemical structure or compound is intended, unless the specific stereochemistry or isomeric form is specifically indicated in the compound name or structure.

General Synthetic Methods for Optimizing the Particle Size of Compounds of Formula (I)

This present crystallization process produces consistently uniform small particles of a compound of Formula (I) with narrow particle size distribution and excellent powder characteristics that facilitate the formulation process and optimal drug product performance. The process eliminates the necessity for jet-milling, resulting in reduced cost and risks associated with sending out valuable API to outside vendors. The process can be used as part of synthesis to directly form small particles of compounds of Formula (I) or as a standalone (recrystallization) process to reduce the particle size of a bulk drug substance with large particle size or agglomerates.

It has been found that these different modifications can be deliberately produced by selecting the solvents used for the crystallization as well as by a suitable choice of the process conditions used in the crystallization process.

In one aspect of the invention, a suitable solvent system for crystallization or recrystallization is methyl ethyl ketone (MEK) or 2-butanone as a solvent and heptane as an antisolvent.

In another aspect of the invention the amount of water in the crystallization solution is from about 0.01 wt % to about 0.5 wt % water in the solution of compound of Formula (I), measured by Karl-Fischer titration (KF). The water amount can, in another embodiment, be from about 0.5 wt % to about 1.2 wt %; in another embodiment, from about 1.2 wt % to about 2.0 wt %.

In one aspect of the invention a suitable temperature for crystallization is about 50° C. The temperature can, in one embodiment, be from about 40° C. to about 60° C.; in another embodiment, from about 30° C. to 50° C.; in another embodiment, from about 50° C. to about the refluxing point of the solvent mixture.

In one aspect of the invention, a suitable particle size is from D90 (equivalent diameter where 90 mass-% of the particles of the powder has a smaller diameter) of about 5 μm to D90 of about 10 μm. The particle size can, in another embodiment, be from D90 of about 10 μm to D90 of about 30 μm; in another embodiment, from D90 of about 30 μm to D90 of about 70 μm.

Description of the Process

The following process is used to crystallize uniform small particles of 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid co-crystal as part of synthesis.

The acetic acid solvate form or anisole solvate form of the free base of 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide (from the preceding step of the synthesis, with <0.2 wt % water in the dry, starting solid) and MEK are heated to 60° C. give a solution, which is polish filtered. Aqueous 85% phosphoric acid is charged at 50° C., followed by heptane, then seed crystals, and another portion of heptane. The batch is cooled linearly to 20° C. over at least 2 hours, aged at 20° C. for at least 2 hours, and filtered. The solid is washed with MEK/heptane (1:2 v/v) and heptane. The solid is dried in the vacuum oven (<100 mmHg, 80° C.) and then de-lumped to give 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid co-crystals.

The particle size of 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid co-crystals from the MEK/heptane process is generally small with D90 (90% of particles having diameter less than) of 5 μm to 25 μm. The control of the particle size by the crystallization process in MEK/heptane is consistent and reliable, as the crystallization of 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid co-crystals in MEK/heptane under the specified conditions has very fast nucleation kinetics which limits particle growth and produces uniformly small particles. Table 1 lists the particle size data for several scale-up batches.

TABLE 1

Particle Size Data for 2-[(3R)-3-(5-Ethanesulfonyl-1H-pyrrolo[2,3-c]pyridin-2-ylmethyl)-4,4,4-trifluoro-3-hydroxy-1,1-dimethylbutyl]-5-fluorobenzamide Phosphoric Acid Co-Crystal Batches

| | Particle Size (μm) | | |
|---|---|---|---|
| Description of Batch | D10 | D50 | D90 |
| Lab batch 1 from acetic acid solvate | 1.29 | 3.42 | 6.49 |
| Lab batch 2 from acetic acid solvate | 1.28 | 3.57 | 7.12 |
| Lab batch 3 from acetic acid solvate | 1.54 | 4.20 | 8.78 |
| Lab batch from new synthesis from acetic acid solvate | 1.17 | 3.19 | 6.24 |
| Pilot plant batch, 9 kg, from acetic acid solvate | 1.26 | 3.35 | 6.35 |
| Kilo lab batch, 1.8 kg, from acetic acid solvate | 1.19 | 2.98 | 5.65 |
| Lab batch, from anisole solvate | 1.31 | 3.70 | 7.03 |
| Pilot plant batch A, 11 kg, from anisole solvate | 1.61 | 4.46 | 9.29 |
| Pilot plant batch B, 22 kg, from anisole solvate | 1.67 | 4.85 | 10.22 |

Note:
The particle size was measured by Sympatec laser light diffraction method.

Production of small particles is typically achieved through maximizing nucleation rate and minimizing growth rate for a given crystallization system. The nucleation and growth rates are independent functions of supersaturation, which is mainly determined by the solubility of the compound in the given solvent system and the initial solution concentration for the process.

In this process, to a solution of 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide with phosphoric acid in MEK (with the initial concentration of approximately 0.11-0.14 g/mL), some heptane, which serves as the antisolvent, (approximately 15 mL/g of the starting material) is added. The effect is the reduction of solubility for 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid co-crystal in the solvent mixture and the creation of supersaturation, which is the driving force for crystallization. The crystallization of 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid co-crystal is then initiated by addition of seed crystals. The crystallization process at this concentration is driven by high degree of supersaturation caused by this MEK/heptane ratio, and very fast nucleation and thus generation of many nuclei are resulted. Due to the fast nucleation rate and the vast number of nuclei generated, the solution quickly becomes depleted and the growth of the nuclei gets limited. The end result is the production of uniformly small particles with D90<10 µm.

In this process, water plays an important role. A small amount of water in the MEK/heptane solution has a significant impact on the solubility of 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid co-crystal in MEK/heptane and therefore affects the supersaturation and the nucleation kinetics of the co-crystal formation. The effect on the nucleation rate directly impacts the particle size of the crystals obtained from the crystallization. The higher the KF, the higher the solubility, therefore, the lower the supersaturation, the slower the kinetics, and the larger the resulting particles.

Figure 1:
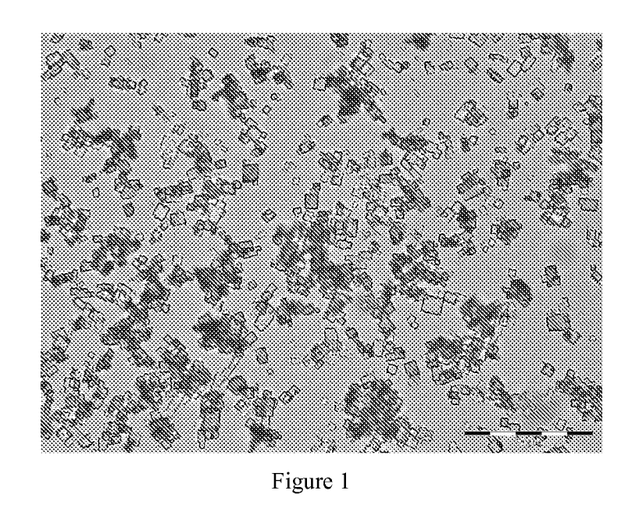
FIG. 1 shows crystals with D90=6 µm from crystallization with 0.1 wt % water (scale bar=50 µm)
Figure 2:
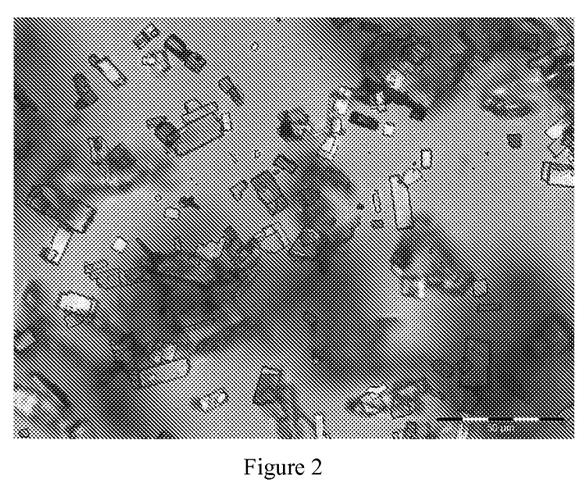
FIG. 2 shows crystals with D90=26 µm from crystallization with 1.1 wt % water (scale bar=50 µm)

When the crystallization is conducted with <0.5 wt % water in the solution, the MEK/heptane ratio can be effectively used as a controlling parameter for the fast nucleation kinetics to obtain small particle size, D90 of approximately 5-10 µm (FIG. 1). When approximately 1.0 wt % water is in the solution (between about 0.7% and 1.2%), the higher solubility of 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid co-crystal in MEK slows the nucleation kinetics and results in larger particles with D90 of approximately 25-30 µm (FIG. 2). When the crystallization is conducted with >1.0 wt % water (between about 1.2 and 2 wt %) in the solution, the resulting particles are larger with D90 of approximately 50 to 70 µm (FIG. 3).

This process can be used to achieve the particle size of desired ranges (for example, anywhere between 5 µm and 50 µm), with the control of water amount in the crystallization solution. The water amount in the solution can be controlled by the proper control of water contents in the starting material (the acetic acid solvate or anisole solvate form of the free base of 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide) and in the solvents used in the process.

Figure 3:
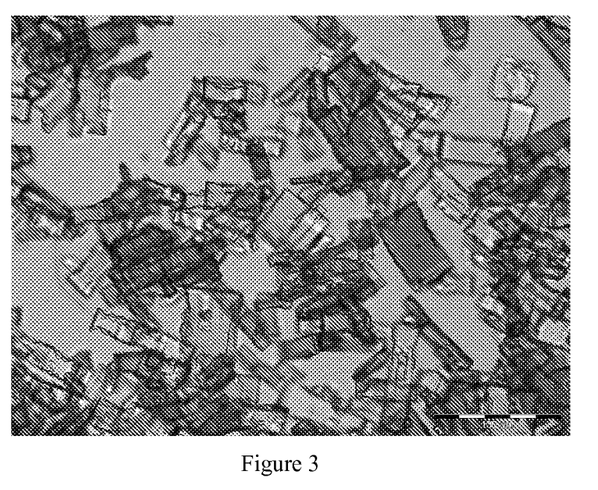
FIG. 3 shows crystals with D90=50 µm from crystallization with 2.0 wt % water (scale bar=100 µm)

FIGS. 1 to 3 show the optical micrographs of the crystals obtained from crystallization with the control of water amount in the solution. Thus, FIG. 1 shows crystals with D90=6 µm from crystallization with 0.1 wt % water (scale bar=50 µm); FIG. 2 shows crystals with D90=26 µm from crystallization with 1.1 wt % water (scale bar=50 µm); and FIG. 3 shows crystals with D90=50 µm from crystallization with 2.0 wt % water (scale bar=100 µm).

Figure 4:
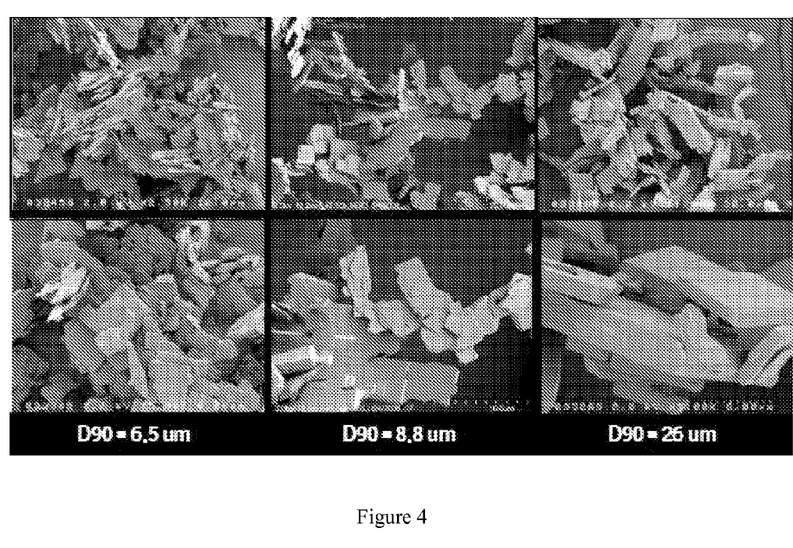
FIG. 4 shows scanning electron microscope (SEM) micrographs of crystals produced from different supersaturation conditions and different water contents.

In addition, FIG. 4 shows scanning electron microscope (SEM) micrographs of crystals produced from different supersaturation conditions and different water contents demonstrating the different particle size of the batch is achievable depending on the process parameter control.

The particles of 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid co-crystal crystallized from this MEK/heptane process show excellent powder properties (flowability, bulk density) compared to the particles produced from other solvent systems.

Experimental Details

The following is a detailed process description to make small particles of 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid co-crystal as part of the synthesis.

The acetic acid solvate form or anisole solvate form of the free base of 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide (50.0 g, 88.2 wt. % free base) is charged to the reactor. MEK (300.0 mL) is added, and the slurry is agitated. The batch is heated to 60° C.±2° C. to dissolve into a clear or slightly hazy solution and passed through a polishing (clarifying) filter while maintaining the solution≧50° C. It is followed by a rinse of 100.0 mL of MEK, preferably heated to 40° C. At this point, KF of the solution is measured to verify <0.2 wt % water in the solution. The batch is heated to 50° C.±2° C. 85% aqueous phosphoric acid (6.067 mL, 10.22 g, 86.1% by titration, 1.05 equiv) is added. The solution remains clear or slightly hazy. Heptane (66.7 mL) is charged slowly (over 15-20 minutes) while maintaining the batch temperature at 50° C.±5° C. The solution remains clear or slightly hazy. The crystal seeds of 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide co-crystal (50.0 mg, 0.1 wt %) suspended in heptane (3.3 mL) are charged. The batch is aged at 50° C.±5° C. for at least 0.5 hour. Crystallization slowly proceeds upon the seed addition. Fully developed crystal slurry is obtained usually in 0.5 hour. Additional heptane (133.3 mL) is charged slowly (over at least 1 hour) at 50° C.±5° C. The batch is cooled to 20° C.±5° C. linearly over at least 2 hours. The slurry is aged at 20° C.±5° C. for at least 2 hours. The slurry is filtered. Filtration is usually very fast. The wet cake is washed with 100 mL of MEK/heptane mixture (1:2 v/v) and rinsed with 100 mL of heptane. The solid is dried at 80° C.±5° C. and <100 mmHg for at least 24 hours (until KF≦0.2% and MEK and heptane≦0.5% (GC analysis)). 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide co-crystal is obtained as a white solid in 86-96% yield with 99.6 area % HPLC purity. The particle size of the product is D90 of about 7 µm.

The following process is a detailed description for a re-crystallization process that can be used as a standalone process to rework a batch with large particles or agglomerates for particle size reduction. The process involves an extraction of the free base from an MEK/water mixture, followed by a phase separation and azeotrope distillation of the MEK solution to reduce the KF to ≦0.2% to ensure production of small particle size. Following the completion of the distillation and concentration adjustment, crystallization of 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide co-crystals is carried out in the typical way by the addition of phosphoric acid and heptane followed by seeding.

2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide co-crystal (50.0 g, 99.6 area % purity) is charged to the reactor. MEK (400 mL) is added, and the slurry is agitated. Water (125 mL) is charged and the batch is heated to 40° C.±2° C. and agitated well to obtain a biphasic solution. The batch is then cooled to 20° C.±2° C. 6.25 mL of NaCl solution (10 wt % aqueous) is added. Agitation is stopped and the phases are allowed settle to clear solutions (for about 2 to 15 hours). The lower aqueous layer is removed. 200 mL of MEK is added and the mixture is distilled at atmospheric pressure while maintaining volume. Initial T is 74.0° C.±0.2° C. Additional MEK is added as necessary until the temperature reaches at least 79.6° C.±0.2° C. The batch is passed through a polishing filter while maintaining the solution≧50° C., followed by a rinse of MEK (100.0 mL, preferably heated to 40° C.). Additional distillation is performed if necessary to adjust the solution volume to approximately 450 mL. At this point, KF of the solution is measured to verify ≦0.2 wt % water in the solution. 85% aqueous phosphoric acid (5.78 mL, 9.74 g, 86.1% by titration, 1.05 equiv) is charged. The solution remains clear or slightly hazy. Heptane (66.7 mL) is charged slowly (over 5-20 minutes) while maintaining the batch temperature at 50° C.±5° C. The solution remains clear or slightly hazy. The crystal seeds of 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide co-crystal (50.0 mg, 0.1 wt %) suspended in heptane (3.3 mL) is charged. The batch is aged at 50° C.±5° C. for at least 0.5 hour. Crystallization slowly proceeds upon the seed addition. Fully developed crystal slurry is obtained usually in 0.5 hour. Additional heptane (133.3 mL) is charged slowly (over at least 1 hour) at 50° C.±5° C. The batch is cooled to 20° C.±5° C. linearly over at least 2 hours. The slurry is aged at 20° C.±5° C. for at least 2 hours. The slurry is filtered. Filtration is usually very fast. The wet cake is washed with 100 mL of MEK/heptane:mixture (1:2 v/v) and rinsed with 100 mL of heptane. The solid is dried at 80° C.±5° C. and ≦100 mmHg for at least 24 hours (until KF≦0.2% and MEK and heptane≦0.5% (GC analysis)). 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide co-crystal is obtained as a white solid in 86-96% yield with 99.6 area % HPLC purity. The particle size of the product is D90 of about 7 μm.

What is claimed is:
1. A process for crystallizing a compound of Formula (I)

(I)

wherein:
$R^1$ is an aryl or heteroaryl group, each optionally independently substituted with one, two, or three substituent groups selected from $C_1$-$C_5$ alkyl, aminocarbonyl, $C_1$-$C_5$ alkylaminocarbonyl, $C_1$-$C_5$ dialkylaminocarbonyl, aminosulfonyl, $C_1$-$C_5$ alkylaminosulfonyl, $C_1$-$C_5$ dialkylaminosulfonyl, halogen, hydroxyl, cyano, and $C_1$-$C_5$ alkylthio wherein the sulfur atom is optionally oxidized to a sulfoxide or sulfone;
$R^2$ is $C_1$-$C_5$ alkylthio wherein the sulfur atom is optionally oxidized to a sulfoxide or sulfone, optionally independently substituted with one, two, or three substituent groups selected from halogen, hydroxy, oxo, cyano, alkoxyalkyl, and aminocarbonyl;
X is CH or N; and
Y is CH or N,
wherein X and Y are not both CH,
or a tautomer, optical isomer, co-crystal, or salt thereof, the process comprising:
(a) dissolving the free base of the compound of Formula (I) in a primary organic solvent to obtain a first solution;
(b) adding an acid to the first solution to obtain a second solution;
(c) combining an organic antisolvent with the second solution to obtain a third solution, wherein the antisolvent is miscible with the primary organic solvent and in which the compound of Formula (I) has a lesser solubility than in the primary organic solvent;
(d) achieving supersaturation of the compound of Formula (I) in the third solution to obtain a supersaturated fourth solution; and
(e) obtaining crystals of the compound of Formula (I) or a tautomer, optical isomer, co-crystal, or salt thereof.

2. The process according to claim 1, wherein the primary organic solvent is a polar organic solvent.

3. The process according to claim 1, wherein the primary organic solvent is MEK, 2-butanone, acetic acid, or a mixture thereof.

4. The process according to claim 3, wherein the primary organic solvent is MEK.

5. The process according to claim 1, wherein the acid is a strong acid.

6. The process according to claim 5, wherein the acid is phosphoric acid.

7. The process according to claim 1, wherein the organic antisolvent is a nonpolar organic solvent.

8. The process according to claim 7, wherein the organic antisolvent is an alkane or cycloalkane.

9. The process according to claim 1, wherein the organic antisolvent is heptane, cyclohexane, methylcyclohexane, or butyl acetate.

10. The process according to claim 1, wherein the ratio of the solubility of the compound of Formula (I) in the primary organic solvent to organic antisolvent is at least 10:1.

11. The process according to claim 1, wherein steps (c) and (d) are achieved by adding the solution in step (b) to the organic antisolvent at a temperature of 0° C. to 40° C.

12. The process according to claim 11, wherein the organic antisolvent includes seed crystals.

13. The process according to claim 1, wherein step (d) is achieved by one or more of the following: adding additional amounts of the organic antisolvent, reducing the temperature, and removing the primary organic solvent.

14. The process according to claim 1, wherein step (e) is accomplished by introducing seed crystals to the supersaturated solution of step (d).

15. The process according to claim 14, further comprising:
(f) adding additional antisolvent to increase the yield of the crystals of the compound of Formula (I) or a tautomer, optical isomer, co-crystal, or salt thereof.

16. The process according to claim 1, wherein the process occurs at a temperature of about 20° C. to about 60° C.

17. The process according to claim 16, wherein the process occurs at a temperature of about 40° C. to about 60° C.

18. The process according to claim 17, wherein the process occurs at a temperature of 30° C. to 50° C.

19. The process according to claim 1, wherein the process occurs at a temperature of about 50° C. to about the refluxing temperature of the fourth solution.

20. The process according to claim 16, wherein the process occurs at a temperature of about 50° C.

21. The process according to claim 1, wherein the third solution includes water.

22. The process according to claim 21, wherein the water present is from about 0.01 wt % to about 0.5 wt % water in the solution of compound of Formula (I), measured by Karl-Fischer titration (KF).

23. The process according to claim 22, wherein the water present is from about 0.5 wt % to about 1.2 wt %.

24. The process according to claim 22, wherein the water present is from about 1.2 wt % to about 2.0 wt %.

25. The process according to claim 23, wherein the water present is selected so that the crystals of the compound of Formula (I) or a tautomer, optical isomer, prodrug, co-crystal, or salt thereof has a D90 of about 5 μm to about 80 μm.

26. The process according to claim 25, wherein the water present is selected so that the crystals of the compound of Formula (I) or a tautomer, optical isomer, prodrug, co-crystal, or salt thereof has a D90 of about 10 μm to about 30 μm.

27. The process according to claim 21, wherein the water present is selected so that the crystals of the compound of Formula (I) or a tautomer, optical isomer, prodrug, co-crystal, or salt thereof has a D90 of about 30 μm to about 70 μm.

28. The process according to claim 1, wherein:
$R^1$ is an aryl or heteroaryl group, each optionally independently substituted with one, two, or three substituent groups selected from $C_1$-$C_5$ alkyl, aminocarbonyl, $C_1$-$C_5$ alkylaminocarbonyl, $C_1$-$C_5$ dialkylaminocarbonyl, aminosulfonyl, $C_1$-$C_5$ alkylaminosulfonyl, $C_1$-$C_5$ dialkylaminosulfonyl, halogen, hydroxyl, cyano, and $C_1$-$C_5$ alkylthio wherein the sulfur atom is optionally oxidized to a sulfoxide or sulfone;
$R^2$ is $C_1$-$C_5$ alkylthio wherein the sulfur atom is optionally oxidized to a sulfoxide or sulfone, each optionally independently substituted with one to three substituent groups selected from halogen, hydroxy, oxo, cyano, alkoxyalkyl, and aminocarbonyl;
X is CH; and
Y is N,
or a tautomer, co-crystal, or salt thereof.

29. The process according to claim 1, wherein:
$R^1$ is an aryl group, optionally substituted with one, two, or three substituent groups independently selected from $C_1$, $C_2$, or $C_3$ alkyl, aminocarbonyl, halogen, and $C_1$, $C_2$, or $C_3$ alkylthio wherein the sulfur atom is optionally oxidized to a sulfoxide or sulfone;
$R^2$ is $C_1$, $C_2$, or $C_3$ alkylthio wherein the sulfur atom is optionally oxidized to a sulfoxide or sulfone, each optionally independently substituted with one to three substituent groups selected from halogen, hydroxy, oxo, cyano, alkoxyalkyl, and aminocarbonyl;
X is CH; and
Y is N,
or a tautomer, co-crystal, or salt thereof.

30. The process according to claim 1, wherein:
$R^1$ is a phenyl group, optionally substituted with one or two substituent groups independently selected from aminocarbonyl, methyl, fluoro, chloro, bromo, and $C_1$ or $C_2$ alkylthio wherein the sulfur atom is optionally oxidized to a sulfoxide or sulfone;
$R^2$ is $C_1$, $C_2$, or $C_3$ alkylthio wherein the sulfur atom is optionally oxidized to a sulfoxide or sulfone;
X is CH; and
Y is N,
or a tautomer, co-crystal, or salt thereof.

31. The process according to claim 1, wherein:
$R^1$ is a phenyl group, optionally substituted with one or two substituent groups independently selected from aminocarbonyl, methyl, fluoro, chloro, bromo, and $C_1$ or $C_2$ alkylthio wherein the sulfur atom is optionally oxidized to a sulfoxide or sulfone;
$R^2$ is $C_1$ or $C_2$ alkylthio wherein the sulfur atom is optionally oxidized to a sulfoxide or sulfone;
X is CH; and
Y is N,
or a tautomer, co-crystal, or salt thereof.

32. The process according to claim 1, wherein the crystals of the compound of Formula (I) is 2-[(3R)-3-(5-ethanesulfonyl-1H-pyrrolo[2,3-c]pyridin-2-ylmethyl)-4,4,4-trifluoro-3-hydroxy-1,1-dimethylbutyl]-5-fluorobenzamide phosphoric acid co-crystal.

* * * * *